(12) United States Patent
Engell et al.

(10) Patent No.: US 9,987,382 B2
(45) Date of Patent: Jun. 5, 2018

(54) RADIOTRACER COMPOSITIONS

(71) Applicant: GE Healthcare Limited, Buckinghamshire (GB)

(72) Inventors: Torgrim Engell, Oslo (NO); Julian Grigg, Amersham (GB); Dimitrios Mantzilas, Oslo (NO)

(73) Assignee: GE HEALTHCARE LIMITED, Buckinghamshire (GB)

( * ) Notice: Subject to any disclaimer, the term of this patent is extended or adjusted under 35 U.S.C. 154(b) by 205 days.

(21) Appl. No.: 14/877,107

(22) Filed: Oct. 7, 2015

(65) Prior Publication Data
US 2016/0022847 A1 Jan. 28, 2016

Related U.S. Application Data

(62) Division of application No. 13/992,800, filed as application No. PCT/EP2011/072352 on Dec. 9, 2011, now Pat. No. 9,180,213.

(60) Provisional application No. 61/421,390, filed on Dec. 9, 2010.

(51) Int. Cl.
| | | |
|---|---|---|
| A61K 51/00 | (2006.01) | |
| A61M 36/14 | (2006.01) | |
| A61K 51/08 | (2006.01) | |
| C07B 59/00 | (2006.01) | |
| A61K 51/04 | (2006.01) | |
| C07K 1/13 | (2006.01) | |

(52) U.S. Cl.
CPC ........ *A61K 51/088* (2013.01); *A61K 51/0497* (2013.01); *A61K 51/082* (2013.01); *C07B 59/008* (2013.01); *C07K 1/13* (2013.01)

(58) Field of Classification Search
CPC ...... A61K 51/00; A61K 51/08; A61K 51/088; A61K 5/04; A61K 51/0497; A61K 51/082; A61K 2123/00; A61K 2121/00; C07K 1/13; C07B 59/008
USPC .......... 424/1.11, 1.49, 1.65, 1.69, 1.81, 1.85, 424/1.89, 9.1, 9.2, 9.3, 9.4, 9.5, 9.6; 514/1, 1.1, 21.1, 21.3, 21.4, 21.5, 21.6, 514/21.8, 21.9; 530/300, 317, 324, 325, 530/326, 327, 328, 329, 330, 331
See application file for complete search history.

(56) References Cited

U.S. PATENT DOCUMENTS

2007/0048217 A1  3/2007  McBride et al.

FOREIGN PATENT DOCUMENTS

| WO | 2006/030291 | 3/2006 |
|---|---|---|
| WO | 2008/098112 | 8/2008 |
| WO | 2009/02914 | 2/2009 |
| WO | 2010/000409 | 1/2010 |
| WO | 2010/079079 | 7/2010 |
| WO | 2010/114723 | 10/2010 |
| WO | 2011/057986 | 5/2011 |
| WO | 2011/060887 | 5/2011 |

OTHER PUBLICATIONS

Poethko et al., J. Nucl. Med., 2004, vol. 45(5), pp. 892-902.
Battle, J. Nucl. Med. Society of Nuclear Medicine Inc., 52(3):424-430, Mar. 1, 2011.
Speranza, Applied Radiation and Isotopes, 67(9):1664-1669, Sep. 2009.
PCT/EP2011/072352 ISRWO dated Apr. 19, 2012.
Li et al. "Site-Specific Labeling of Annexin V with F-18 for Apoptosis Imaging", Bioconjugate Chem, 16:1684-1688 (2008).
Office Action (translation and original) issued in corresponding CN Application No. 201180059092.5 entitled Radiotracer Compositions (dated Oct. 9, 2015).

*Primary Examiner* — D L Jones
(74) *Attorney, Agent, or Firm* — Wood IP LLC

(57) ABSTRACT

The present invention relates to improved radiotracer imaging agent compositions, which comprises $^{18}$F-labelled biological targeting moieties, wherein impurities which affect imaging in vivo are identified and suppressed. Also provided are radiopharmaceuticals comprising said improved compositions, together with radiofluorinated aldehyde compositions useful in preparing said radiotracer compositions. The invention also includes methods of imaging and/or diagnosis using the radiopharmaceutical compositions described.

20 Claims, No Drawings

RADIOTRACER COMPOSITIONS

FIELD OF THE INVENTION

The present invention relates to improved radiotracer imaging agent compositions, which comprises $^{18}$F-labelled biological targeting moieties, wherein impurities which affect imaging in vivo are identified and suppressed. Also provided are radiopharmaceuticals comprising said improved compositions, together with radiofluorinated aldehyde compositions useful in preparing said radiotracer compositions. The invention also includes methods of imaging and/or diagnosis using the radiopharmaceutical compositions described.

BACKGROUND TO THE INVENTION

WO 2004/080492 discloses a method of radiofluorination of a vector which comprises reaction of a compound of formula (I) with a compound of formula (II):

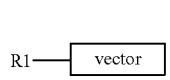
(I)

(II)

or a compound of formula (III) with a compound of formula (IV)

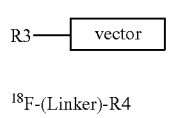
(III)

(IV)

wherein:
R1 is an aldehyde moiety, a ketone moiety, a protected aldehyde such as an acetal, a protected ketone, such as a ketal, or a functionality, such as diol or N-terminal serine residue, which can be rapidly and efficiently oxidised to an aldehyde or ketone using an oxidising agent;
R2 is a group selected from primary amine, secondary amine, hydroxylamine, hydrazine, hydrazide, aminoxy, phenylhydrazine, semicarbazide, and thiosemicarbazide and is preferably a hydrazine, hydrazide or aminoxy group;
R3 is a group selected from primary amine, secondary amine, hydroxylamine, hydrazine, hydrazide, aminoxy, phenylhydrazine, semicarbazide, or thiosemicarbazide, and is preferably a hydrazine, hydrazide or aminoxy group;
R4 is an aldehyde moiety, a ketone moiety, a protected aldehyde such as an acetal, a protected ketone, such as a ketal, or a functionality, such as diol or N-terminal serine residue, which can be rapidly and efficiently oxidised to an aldehyde or ketone using an oxidising agent;
to give a conjugate of formula (V) or (VI) respectively:

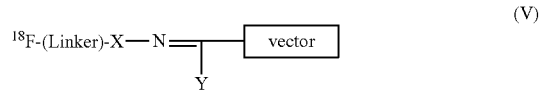
(V)

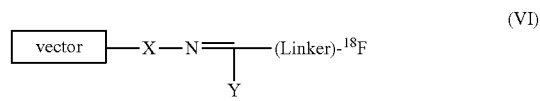
(VI)

wherein X is —CO—NH—, —NH—, —O—, —NHCONH—, or —NHCSNH—, and is preferably —CO—NH—, —NH— or —O—; Y is H, alkyl or aryl substituents; and the Linker group in the formulae (II), (IV), (V) and (VI) is selected from:

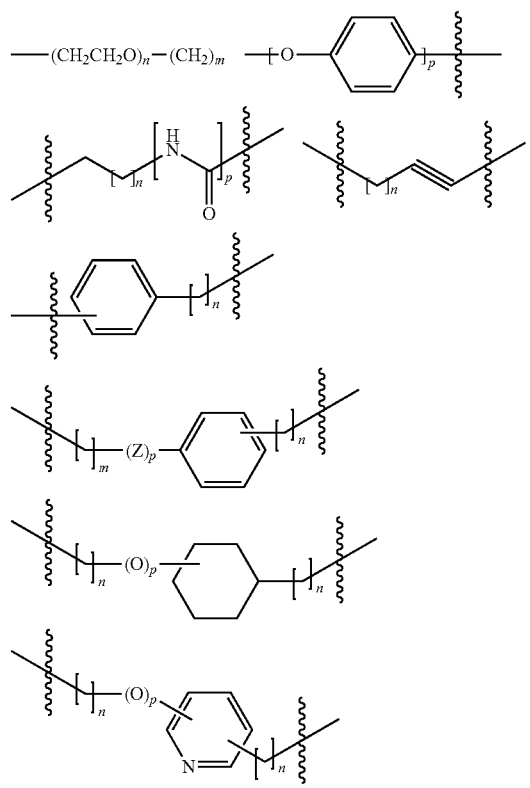

wherein n is an integer of 0 to 20; m is an integer of 1 to 10; p is an integer of 0 or 1; Z is O or S.

WO 2006/030291 discloses a method for radiofluorination comprising reaction of a compound of formula (I):

(I)

wherein the vector comprises the fragment:

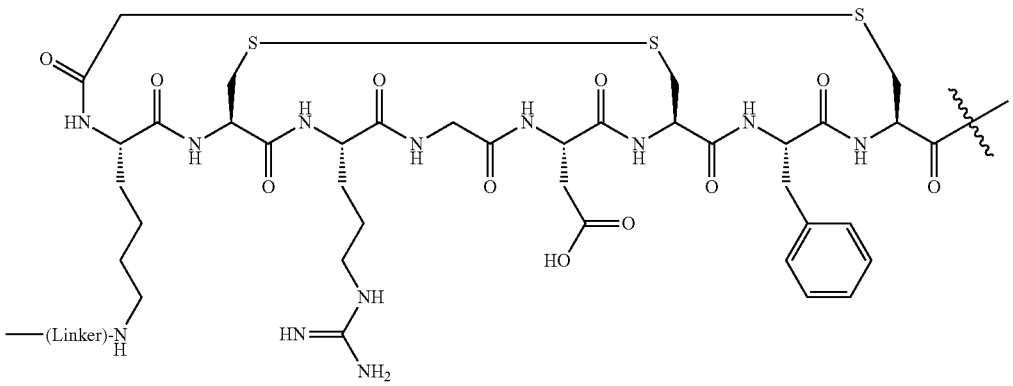

with a compound of formula (II):

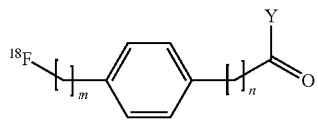

(II)

wherein:
n is an integer of 0 to 20;
m is an integer of 0 to 10;
Y is hydrogen, $C_{1-6}$alkyl, or phenyl
to give a compound of formula (III):

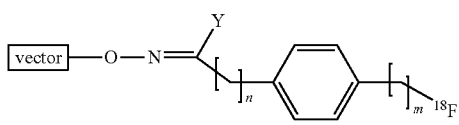

(III)

wherein m, n, and Y are defined as for the compound of formula (II) and the vector is as defined for the compound of formula (I).

Glaser et al [Bioconj. Chem., 19(4), 951-957 (2008)], describe the synthesis of $^{18}$F-labelled aldehydes, including $^{18}$F-fluorobenzaldehyde, and their conjugation to amino-oxy functionalised cyclic RGD peptides.

Speranza et al [Appl. Rad. Isotop., 67, 1664-1669 (2009)] describe an automated synthesis of [$^{18}$F]-fluorobenzaldehyde ([$^{18}$F]-FBA) using a TRACERlab™ apparatus. A handmade purification device is used to purify the [$^{18}$F]-FBA. Speranza et al describe the fact that cartridge purification is preferred over HPLC purification for automated synthesizer apparatus syntheses. Their cartridge methodology, however, suggests that dichloromethane or chloroform are the best solvents for [$^{18}$F]-FBA purification. Both solvents have unsuitable toxicological properties for in vivo use, and are immiscible with water. The method is therefore unsuitable for radiopharmaceutical preparations.

Battle et al [J. Nucl. Med., 52(3), 424-430 (2011)] disclose monitoring anti-angiogenic therapy with [$^{18}$F]-fluciclatide:

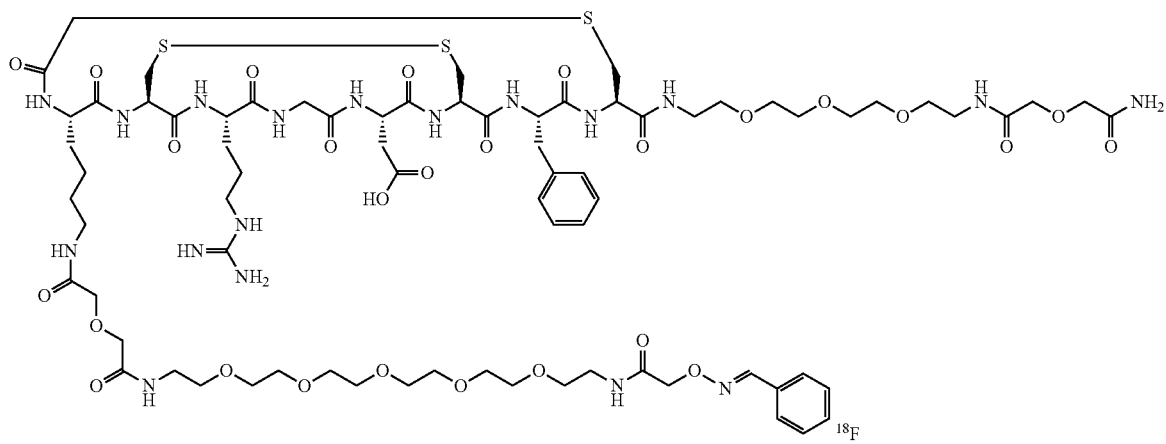

[$^{18}$F]-fluciclat

Battle et al mention that the [$^{18}$F]-FBA used was purified by diluting with water, and trapping on a solid-phase extraction (SPE) cartridge. Impurities such as precursor, DMSO, Kryptofix-222 and hydrophilic by-products were said to be eluted to waste, and the [$^{18}$F]-FBA subsequently eluted with ethanol. The present inventors have, however, found that using a C18 SPE cartridge only some of the precursor is eluted to waste, and the remainder co-elutes when the [$^{18}$F]-FBA is eluted with ethanol.

There is therefore still a need for alternative methods of labelling biological targeting moieties with $^{18}$F.

The Present Invention

The present invention provides improved $^{18}$F-radiolabelled biological targeting moiety (BTM) compositions, derived from the conjugation of $^{18}$F-labelled aldehydes. To aminooxy- or hydrazine-functionalised BTMs. The invention is based on detailed analyses of the impurities present in such aldehydes, and an understanding of how they may be carried through into the radiolabelled BTM product—plus how best to suppress all undesired impurity species. Many of these impurities were not recognised in the prior art, and hence such prior art agents contained undesirable species which would adversely affect the imaging characteristics.

In addition, the improved compositions of the present inventions can be achieved in shorter preparation times, which minimises any loss of $^{18}$F (half-life 109 minutes) radioactive content during the preparation and purification steps prior to use. The compositions of the present invention can be obtained using methodology which is amenable to automation on a commercial automated synthesizer apparatus—an advantage over prior art HPLC methods (which cannot be automated in this way). Automation confers improved reproducibility, as well as reduced operator radiation dose.

In addition, the higher radiochemical yield and purity of the product means that less functionalised BTM need be used in obtain the same amount of radioactive product. Since the unlabelled BTM will compete for the same biological site in vivo, lowering the amount of functionalised BTM present helps preserve the efficacy of the radiolabelled product. In addition, since the BTM may be e.g. a complex polypeptide or protein which is expensive and time-consuming to obtain, that is an important efficiency of time/materials.

The present invention provides compositions wherein the concentration of the desired $^{18}$F-radiofluorinated BTM is enhanced by a factor of about 40, while the chemical impurities are reduced by about 99% (ie. by a factor of about 100).

DETAILED DESCRIPTION OF THE INVENTION

In a first aspect, the present invention provides a composition which comprises an imaging agent of Formula (I) together with one or more non-radioactive awl derivatives of Formula (II):

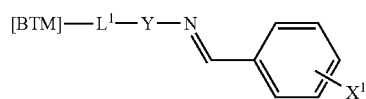
(I)

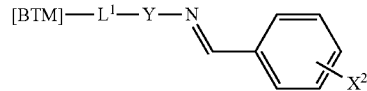
(II)

wherein:
BTM is the biological targeting molecule;
L$^1$ is a synthetic linker group of formula -(A)$_m$- wherein each A is independently —CR$_2$—, —CR═CR—, —C≡C—, —CR$_2$CO$_2$—, —CO$_2$CR$_2$—, —NRCO—, —CONR—, —NR(C═O)NR—, —NR(C═S)NR—, —SO$_2$NR—, —NRSO$_2$—, —CR$_2$OCR$_2$—, —CR$_2$SCR$_2$—, —CR$_2$NRCR$_2$—, a C$_{4-8}$ cycloheteroalkylene group, a C$_{4-8}$ cycloalkylene group, —Ar—, —NR—Ar—, —O—Ar—, —Ar—(CO)—, an amino acid, a sugar or a monodisperse polyethyleneglycol (PEG) building block, wherein each Ar is independently a C$_{5-12}$ arylene group, or a C$_{3-12}$ heteroarylene group;
each R is independently chosen from H, C$_{1-4}$ alkyl, C$_{2-4}$ alkenyl, C$_{2-4}$ alkynyl, C$_{1-4}$ alkoxyalkyl or C$_{1-4}$ hydroxyalkyl;
m is an integer of value 1 to 20;
Y is —O— or —NH—;
X$^1$ is $^{18}$F, —O(CH$_2$)$_q$$^{18}$F or —OCH$_2$—CH(OH)—CH$_2$$^{18}$F, wherein q is 2, 3 or 4,
X$^2$ is —N$^+$(CH$_3$)$_3$, —N(CH$_3$)$_2$, —OCH$_3$, H, —CH$_3$, —OH, —SCH$_3$, —OC$_6$H$_4$CHO or $^{19}$F,
wherein BTM, L$^1$ and Y are the same in Formula (I) and (II);
and wherein the total concentration of derivatives of Formula (II) present in the composition is less than 150 µg/mL.

The term "composition" has its conventional meaning and refers to a mixture of the radiolabelled BTM of Formula (I), with one or more non-radioactive aryl derivatives of Formula (II). Multiple derivatives of Formula (II) may be present in the composition—but in Formulae (I) and (II) BTM, L$^1$ and Y are the same for all components of the composition, and X$^1$ and X$^2$ are located at the same ortho, meta or para-position on the phenyl ring relative to the —C═N group. The components of the composition of the first aspect therefore differ only in the identity of X$^1$ and X$^2$.

The term "concentration of derivatives of Formula (II) present" refers to the total concentration of all compounds of Formula (II) present, even though X$^2$ may differ. As an illustration, present Example 2 uses 3.3 mg of trimethylammonium benzaldehyde precursor in 1.1 mL volume (3.0 mg/mL or 3000 µg/mL). 77 GBq of [$^{18}$F]-fluorobenzaldehyde equates to approximately 0.072 Hence, in chemical terms, the [$^{18}$F]-fluoride consumes a relatively small proportion of the precursor, and without the methods of the present invention, the level of Formula (II) impurities would be significantly greater. The level of less than 150 µg/mL requires that at least 90%, preferably at least 95% of such impurities present have been removed. Preferably the concentration of derivatives of Formula (II) present is less than 100 µg/mL, more preferably less than 45 µg/mL. Quantification is by HPLC-MS, by reference to a calibration curve based on authentic samples of known impurities. The extinction coefficients of authentic samples were also determined to aid quantification. When X$^2$ is $^{19}$F, that corresponds to any $^{19}$F carrier present in the $^{18}$F radioisotope used. Such species contribute to the non-radioactive impurities of Formula (II).

The terms "comprising" or "comprises" have their conventional meaning throughout this application and imply that the composition must have the components listed, but that other, unspecified compounds or species may be present in addition. The terms therefore include as a preferred subset "consisting essentially of" which means that the composition has the components listed without other compounds or species being present.

The imaging agent of Formula (I) comprises a radiofluorinated biological targeting moiety (BTM). By the term "imaging agent" is meant a compound suitable for imaging the mammalian body. Preferably, the mammal is an intact mammalian body in vivo, and is more preferably a human subject. Preferably, the imaging agent can be administered to the mammalian body in a minimally invasive manner, i.e. without a substantial health risk to the mammalian subject when carried out under professional medical expertise. Such minimally invasive administration is preferably intravenous administration into a peripheral vein of said subject, without the need for local or general anaesthetic.

The term "in vivo imaging" as used herein refers to those techniques that non-invasively produce images of all or part of an internal aspect of a mammalian subject. A preferred imaging technique of the present invention is positron emission tomography (PET).

By the term "biological targeting moiety" (BTM) is meant a compound which, after administration, is taken up selectively or localises at a particular site of the mammalian body in vivo. Such sites may be implicated in a particular disease state or be indicative of how an organ or metabolic process is functioning.

By the term "amino acid" is meant an L- or D-amino acid, amino acid analogue (eg. naphthylalanine) which may be naturally occurring or of purely synthetic origin, and may be optically pure, i.e. a single enantiomer and hence chiral, or a mixture of enantiomers. Conventional 3-letter or single letter abbreviations for amino acids are used herein. Preferably the amino acids of the present invention are optically pure.

By the term "sugar" is meant a mono-, di- or tri-saccharide. Suitable sugars include: glucose, galactose, maltose, mannose, and lactose. Optionally, the sugar may be functionalised to permit facile coupling to amino acids. Thus, eg. a glucosamine derivative of an amino acid can be conjugated to other amino acids via peptide bonds. The glucosamine derivative of asparagine (commercially available from NovaBiochem) is one example of this:

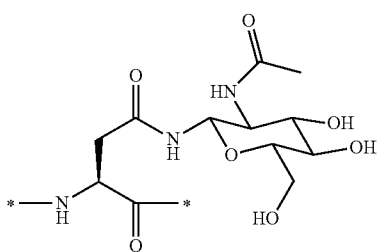 [SMILES: CN[C@@H](CC(=O)NC1OC(CO)C(O)C(O)C1NC(C)=O)C(C)=O]

The term "polyethyleneglycol polymer" or "PEG" has its conventional meaning, as described e.g. in "The Merck Index", 14th Edition entry 7568, i.e. a liquid or solid polymer of general formula $H(OCH_2CH_2)_nOH$ where n is an integer greater than or equal to 4. The polyethyleneglycol polymers of the present invention may be linear or branched, but are preferably linear. The polymers are also preferably non-dendrimeric. Preferred PEG-containing linker groups comprise units derived from oligomerisation of the monodisperse PEG-like structures of Formulae Bio1 or Bio2:

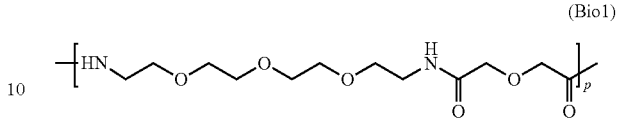

17-amino-5-oxo-6-aza-3,9,12,15-tetraoxaheptadecanoic acid of Formula Bio1 wherein p is an integer from 1 to 10. Alternatively, a PEG-like structure based on a propionic acid derivative of Formula Bio2 can be used:

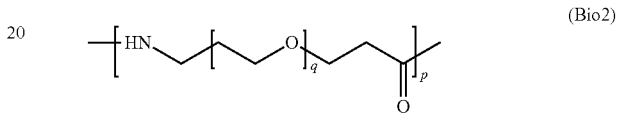

where p is as defined for Formula Bio1 and q is an integer from 3 to 15.

In Formula Bio2, p is preferably 1 or 2, and q is preferably 5 to 12.

In Formulae (I) and (II), isomerism at the C=N bond means that E- or Z-diastereomers may occur. Although drawn as only a single isomer, Formulae (I) and (II) are intended to encompass mixtures of such isomers, as well as mixtures enriched in one such diastereomer, as well as pure diastereomers.

Preferred Embodiments

In Formulae (I) of the first aspect, $X^1$ is preferably $^{18}F$, or $-O(CH_2)_q{}^{18}F$ where q is 2 or 3; more preferably $^{18}F$ or $-O(CH_2)_3{}^{18}F$, most preferably $^{18}F$.

In Formulae (I) and (II) of the first aspect, $X^1$ and $X^2$ are preferably located at either the ortho or para-position, more preferably at the para-position.

In Formulae (I) and (II), Y is preferably —O—. More preferably, Y is —O— and $X^1$ and $X^2$ are preferably located at the para-position. For each such combination, preferred BTM groups are as described below.

The BTM may be of synthetic or natural origin, but is preferably synthetic. The term "synthetic" has its conventional meaning, i.e. man-made as opposed to being isolated from natural sources eg. from the mammalian body. Such compounds have the advantage that their manufacture and impurity profile can be fully controlled. Monoclonal antibodies and fragments thereof of natural origin are therefore outside the scope of the term 'synthetic' as used herein. The BTM is preferably non-proteinaceous, i.e. does not comprise a protein.

The molecular weight of the BTM is preferably up to 10,000 Daltons. More preferably, the molecular weight is in the range 200 to 9,000 Daltons, most preferably 300 to 8,000 Daltons, with 400 to 6,000 Daltons being especially preferred. When the BTM is a non-peptide, the molecular weight of the BTM is preferably up to 3,000 Daltons, more preferably 200 to 2,500 Daltons, most preferably 300 to 2,000 Daltons, with 400 to 1,500 Daltons being especially preferred.

The biological targeting moiety preferably comprises: a 3-80 mer peptide, peptide analogue, peptoid or peptide mimetic which may be a linear or cyclic peptide or combination thereof; a single amino acid; an enzyme substrate, enzyme antagonist enzyme agonist (including partial agonist) or enzyme inhibitor; receptor-binding compound (including a receptor substrate, antagonist, agonist or substrate); oligonucleotides, or oligo-DNA or oligo-RNA fragments.

By the term "peptide" is meant a compound comprising two or more amino acids, as defined below, linked by a peptide bond (i.e. an amide bond linking the amine of one amino acid to the carboxyl of another). The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. The term "peptide analogue" refers to peptides comprising one or more amino acid analogues, as described below. See also *Synthesis of Peptides and Peptidomimetics*, M. Goodman et al, Houben-Weyl Vol E22c of *Methods in Organic Chemistry*, Thieme (2004).

When the BTM is an enzyme substrate, enzyme antagonist, enzyme agonist, enzyme inhibitor or receptor-binding compound it is preferably a non-peptide, and more preferably is synthetic. By the term "non-peptide" is meant a compound which does not comprise any peptide bonds, i.e. an amide bond between two amino acid residues. Suitable enzyme substrates, antagonists, agonists or inhibitors include glucose and glucose analogues such as fluorodeoxyglucose; fatty acids, or elastase, Angiotensin II or metalloproteinase inhibitors. A preferred non-peptide Angiotensin II antagonist is Losartan. Suitable synthetic receptor-binding compounds include estradiol, estrogen, progestin, progesterone and other steroid hormones; ligands for the dopamine D-1 or D-2 receptor, or dopamine transporter such as tropanes; and ligands for the serotonin receptor.

The BTM is most preferably a 3-100 mer peptide or peptide analogue. When the BTM is a peptide, it is preferably a 4-30 mer peptide, and most preferably a 5 to 28-mer peptide. When the BTM is a peptide, preferred such peptides include:

somatostatin, octreotide and analogues, peptides which bind to the ST receptor, where ST refers to the heat-stable toxin produced by *E. coli* and other micro-organisms;

bombesin;

vasoactive intestinal peptide;

neurotensin;

laminin fragments eg. YIGSR, PDSGR, IKVAV, LRE and KCQAGTFALRGDPQG,

N-formyl chemotactic peptides for targeting sites of leucocyte accumulation,

Platelet factor 4 (PF4) and fragments thereof,

RGD (Arg-Gly-Asp)-containing peptides, which may eg. target angiogenesis [R. Pasqualini et al., Nat Biotechnol. 1997 June; 15(6):542-6]; [E. Ruoslahti, Kidney Int. 1997 May; 51(5):1413-7].

peptide fragments of $\alpha_2$-antiplasmin, fibronectin or beta-casein, fibrinogen or thrombospondin. The amino acid sequences of $\alpha_2$-antiplasmin, fibronectin, beta-casein, fibrinogen and thrombospondin can be found in the following references: $\alpha_2$-antiplasmin precursor [M. Tone et al., J. Biochem, 102, 1033, (1987)]; beta-casein [L. Hansson et al, Gene, 139, 193, (1994)]; fibronectin [A. Gutman et al, FEBS Lett., 207, 145, (1996)]; thrombospondin-1 precursor [V. Dixit et al, Proc. Natl. Acad. Sci., USA, 83, 5449, (1986)]; R. F. Doolittle, Ann. Rev. Biochem., 53, 195, (1984);

peptides which are substrates or inhibitors of angiotensin, such as:

angiotensin II Asp-Arg-Val-Tyr-Ile-His-Pro-Phe (E. C. Jorgensen et al, *J. Med. Chem.*, 1979, Vol 22, 9, 1038-1044)

[Sar, Ile] Angiotensin II: Sar-Arg-Val-Tyr-Ile-His-Pro-Ile (R. K. Turker et al., *Science*, 1972, 177, 1203).

Angiotensin I: Asp-Arg-Val-Tyr-Ile-His-Pro-Phe-His-Leu.

When the BTM is a peptide, one or both termini of the peptide, preferably both, have conjugated thereto a metabolism inhibiting group ($M^{IG}$). Having both peptide termini protected in this way is important for in vivo imaging applications, since otherwise rapid metabolism would be expected with consequent loss of selective binding affinity for the BTM peptide. By the term "metabolism inhibiting group" ($M^{IG}$) is meant a biocompatible group which inhibits or suppresses enzyme, especially peptidase such as carboxypeptidase, metabolism of the BTM peptide at either the amino terminus or carboxy terminus. Such groups are particularly important for in vivo applications, and are well known to those skilled in the art and are suitably chosen from, for the peptide amine terminus:

N-acylated groups —NH(C=O)$R^G$ where the acyl group —(C=O)$R^G$ has $R^G$ chosen from: $C_{1-6}$ alkyl, $C_{3-10}$ aryl groups or comprises a polyethyleneglycol (PEG) building block. Suitable PEG groups are described for the linker group ($L^1$), above. Preferred such PEG groups are the biomodifiers of Formulae Bio1 or Bio2 (above). Preferred such amino terminus $M^{IG}$ groups are acetyl, benzyloxycarbonyl or trifluoroacetyl, most preferably acetyl.

Suitable metabolism inhibiting groups for the peptide carboxyl terminus include: carboxamide, tert-butyl ester, benzyl ester, cyclohexyl ester, amino alcohol or a polyethyleneglycol (PEG) building block. A suitable $M^{IG}$ group for the carboxy terminal amino acid residue of the BTM peptide is where the terminal amine of the amino acid residue is N-alkylated with a $C_{1-4}$ alkyl group, preferably a methyl group. Preferred such $M^{IG}$ groups are carboxamide or PEG, most preferred such groups are carboxamide.

Preferred BTM peptides are RGD peptides. A more preferred such RGD peptide comprises the fragment:

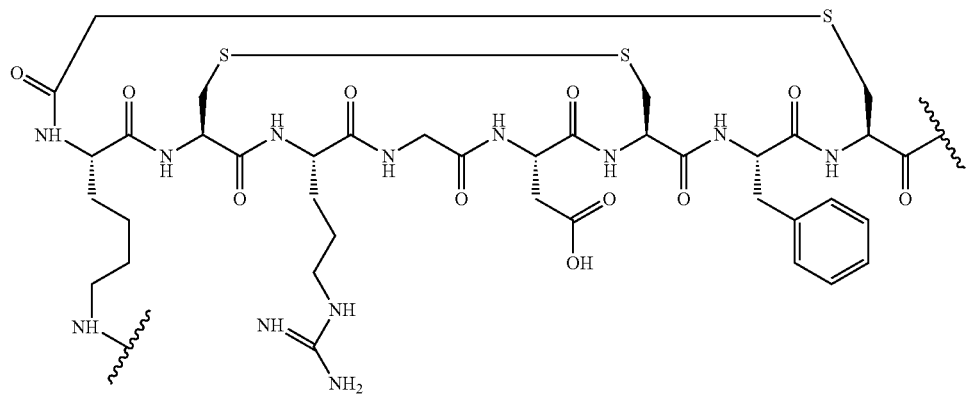 [SMILES: *NCCCC[C@@H]1NC(=O)CSC[C@@H](C(*)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]
A most preferred such RGD peptide is when the BTM is a peptide of Formula (BTM1):
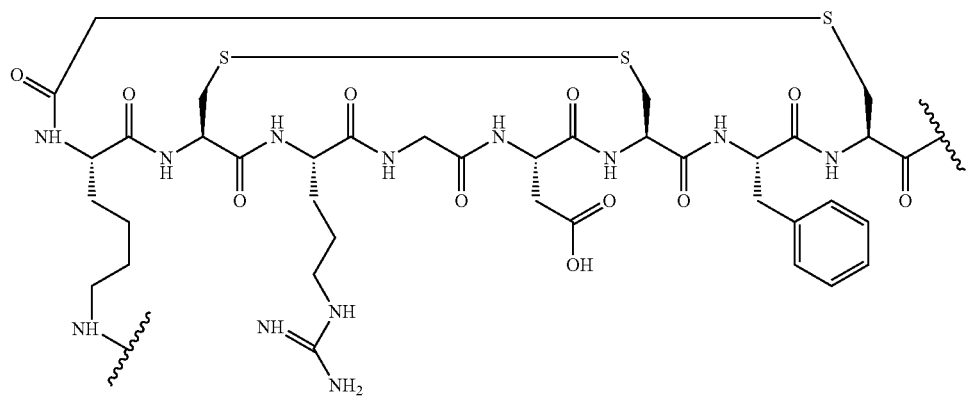
wherein $X^7$ is either —NH$_2$ or PEG1, wherein PEG1 is:
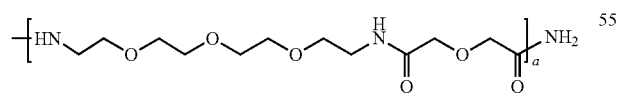
wherein a is an integer of from 1 to 10.

In Formula BTM1, $X^7$ is preferably PEG1 with 'a' preferably equal to 1.

A preferred imaging agent of Formula (I) is [$^{18}$F]-fluciclatide of Formula (IA):

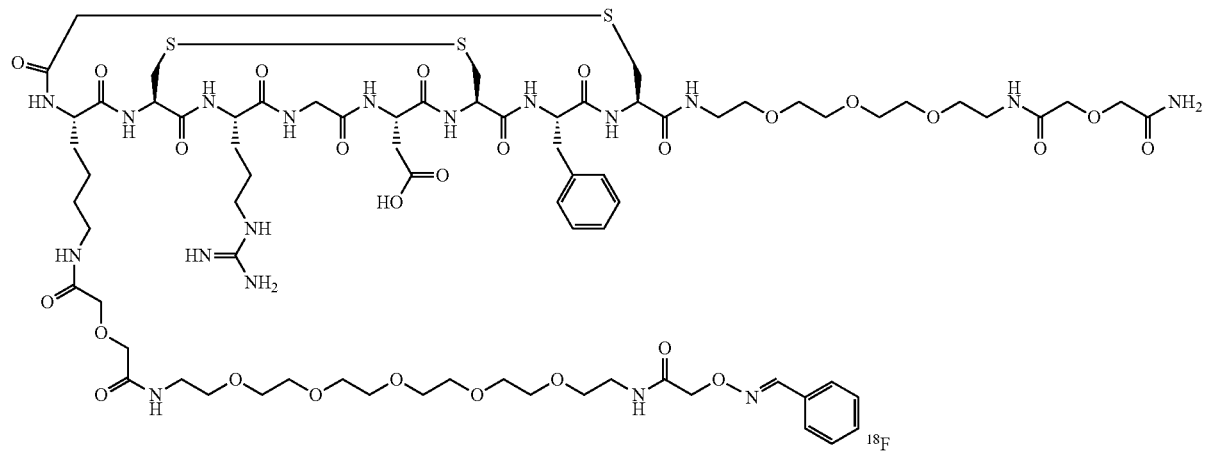

(IA)

In the composition of the first aspect, when $X^1$ is $^{18}$F, $X^2$ is preferably —N$^+$(CH$_3$)$_3$, —N(CH$_3$)$_2$ or —OH, more preferably multiple derivatives of Formula (II) are present such that $X^2$ is equal to all 3 of these groups. That is described more fully in the third aspect (below).

Preferably, the imaging agent composition is provided in sterile form, i.e. in a form suitable for mammalian administration as is described in the second aspect (below).

The imaging agent compositions of the first aspect can be obtained as described in the fourth aspect (below).

In a second aspect, the present invention provides a radiopharmaceutical composition which comprises the imaging agent composition of the first aspect, together with a biocompatible carrier, in a form suitable for mammalian administration.

Preferred aspects of the imaging agent composition in the second aspect are as defined in the first aspect (above).

By the phrase "in a form suitable for mammalian administration" is meant a composition which is sterile, pyrogen-free, lacks compounds which produce toxic or adverse effects, and is formulated at a biocompatible pH (approximately pH 4.0 to 10.5). Such compositions lack particulates which could risk causing emboli in vivo, and are formulated so that precipitation does not occur on contact with biological fluids (e.g. blood). Such compositions also contain only biologically compatible excipients, and are preferably isotonic.

The "biocompatible carrier" is a fluid, especially a liquid, in which the imaging agent can be suspended or preferably dissolved, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is isotonic); an aqueous buffer solution comprising a biocompatible buffering agent (e.g. phosphate buffer); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). Preferably the biocompatible carrier is pyrogen-free water for injection, isotonic saline or phosphate buffer.

The imaging agents and biocompatible carrier are each supplied in suitable vials or vessels which comprise a sealed container which permits maintenance of sterile integrity and/or radioactive safety, plus optionally an inert headspace gas (eg. nitrogen or argon), whilst permitting addition and withdrawal of solutions by syringe or cannula. A preferred such container is a septum-sealed vial, wherein the gas-tight closure is crimped on with an overseal (typically of aluminium). The closure is suitable for single or multiple puncturing with a hypodermic needle (e.g. a crimped-on septum seal closure) whilst maintaining sterile integrity. Such containers have the additional advantage that the closure can withstand vacuum if desired (eg. to change the headspace gas or degas solutions), and withstand pressure changes such as reductions in pressure without permitting ingress of external atmospheric gases, such as oxygen or water vapour.

Preferred multiple dose containers comprise a single bulk vial (e.g. of 10 to 50 cm$^3$ volume) which contains multiple patient doses, whereby single patient doses can thus be withdrawn into clinical grade syringes at various time intervals during the viable lifetime of the preparation to suit the clinical situation. Pre-filled syringes are designed to contain a single human dose, or "unit dose" and are therefore preferably a disposable or other syringe suitable for clinical use. The pharmaceutical compositions of the present invention preferably have a dosage suitable for a single patient and are provided in a suitable syringe or container, as described above.

The pharmaceutical composition may contain additional optional excipients such as: an antimicrobial preservative, pH-adjusting agent, filler, radioprotectant, solubiliser or osmolality adjusting agent. By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (i.e. 4-aminobenzoic acid), gentisic acid (i.e. 2,5-dihydroxybenzoic acid) and salts thereof with a biocompatible cation. By the term "biocompatible cation" (B$^c$) is meant a positively charged counterion which forms a salt with an ionised, negatively charged group, where said positively charged counterion is also non-toxic and hence suitable for administration to the mammalian body, especially the human body. Examples of suitable biocompatible cations include: the alkali metals sodium or potassium; the alkaline earth metals calcium and magnesium; and the ammonium ion. Preferred biocompatible cations are sodium and potassium, most preferably sodium.

When the radiopharmaceutical composition comprises fluciclatide of Formula (IA), the composition preferably comprises a radioprotectant. Preferably, the radioprotectant is sodium 4-aminobenzoate (Na-pABA). A preferred concentration of Na-pABA to use is 1 to 3 mg/mL, preferably 1.5 to 2.5 mg/mL, most preferably about 2.0 mg/mL.

By the term "solubiliser" is meant an additive present in the composition which increases the solubility of the imaging agent in the solvent. A preferred such solvent is aqueous media, and hence the solubiliser preferably improves solubility in water. Suitable such solubilisers include: $C_{1-4}$ alcohols; glycerine; polyethylene glycol (PEG); propylene glycol; polyoxyethylene sorbitan monooleate; sorbitan monooloeate; polysorbates; poly(oxyethylene)poly(oxypropylene)poly(oxyethylene) block copolymers (Pluronics™); cyclodextrins (e.g. alpha, beta or gamma cyclodextrin, hydroxypropyl-β-cyclodextrin or hydroxypropyl-γ-cyclodextrin) and lecithin.

By the term "antimicrobial preservative" is meant an agent which inhibits the growth of potentially harmful micro-organisms such as bacteria, yeasts or moulds. The antimicrobial preservative may also exhibit some bactericidal properties, depending on the dosage employed. The main role of the antimicrobial preservative(s) of the present invention is to inhibit the growth of any such micro-organism in the pharmaceutical composition. The antimicrobial preservative may, however, also optionally be used to inhibit the growth of potentially harmful micro-organisms in one or more components of kits used to prepare said composition prior to administration. Suitable antimicrobial preservative(s) include: the parabens, i.e. methyl, ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the composition is within acceptable limits (approximately pH 4.0 to 10.5) for human or mammalian administration. Suitable such pH-adjusting agents include pharmaceutically acceptable buffers, such as tricine, phosphate or TRIS [i.e. tris(hydroxymethyl)aminomethane], and pharmaceutically acceptable bases such as sodium carbonate, sodium bicarbonate or mixtures thereof. When the composition is employed in kit form, the pH adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

The radiopharmaceutical compositions of the fourth aspect may be prepared under aseptic manufacture (i.e. clean room) conditions to give the desired sterile, non-pyrogenic product. It is preferred that the key components, especially the associated reagents plus those parts of the apparatus which come into contact with the imaging agent (eg. vials) are sterile. The components and reagents can be sterilised by methods known in the art, including: sterile filtration, terminal sterilisation using e.g. gamma-irradiation, autoclaving, dry heat or chemical treatment (e.g. with ethylene oxide). It is preferred to sterilise some components in advance, so that the minimum number of manipulations needs to be carried out. As a precaution, however, it is preferred to include at least a sterile filtration step as the final step in the preparation of the pharmaceutical composition.

The radiopharmaceutical compositions of the present invention may be prepared as described in the fourth aspect (below).

In a third aspect, the present invention provides a composition which comprises a radioactive aldehyde of Formula (A) together with one or more non-radioactive aldehydes of Formula (B):

wherein $X^1$ and $X^2$ are as defined in the first aspect;
and wherein the total concentration of derivatives of Formula (B) present in the composition is less than 150 μg/mL.

Preferred aspects of $X^1$ and $X^2$ in the third aspect are as defined in the first aspect (above). Preferably the concentration of derivatives of Formula (B) present is less than 100 μg/mL, more preferably less than 45 μg/mL.

In the composition of the third aspect, $X^1$ is preferably $^{18}F$ and $X^2$ is —$N^+(CH_3)_3$, —$N(CH_3)_2$ or —OH or combinations thereof.

Thus, the present inventors have found that, when [$^{18}F$]-fluorobenzaldehyde ([$^{18}F$]-FBA) is prepared by conventional radiosynthesis from TMAB, over 95% of the chemical impurities present are derived from TMAB, DMAB and HBA:

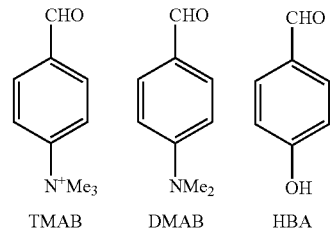

In addition, impurities of Formula (II) can arise where $X^2$=—$SCH_3$ or —$OC_6H_4CHO$. The $X^2$=—$SCH_3$ species can arise when DMSO is used as the solvent. These impurities have been identified by LC-MS studies.

Since these impurities are all aldehydic in nature, they compete with [$^{18}F$]-FBA with the functionalised BTM of interest. That has three important effects:
 (i) the radioactive yield is reduced;
 (ii) the overall chemical purity is reduced;
 (iii) the imaging agent composition arising therefrom may contain multiple BTM-functionalised impurities [of Formula (II)] which may compete with the $^{18}$F-labelled imaging agent for the desired biological site in vivo.

Issue (iii) may therefore impact on the effectiveness of the imaging agent in vivo. In addition, since the BTM conjugates of Formulae (I) and (II) are of similar structure, they can be difficult to separate once formed and present in the composition. The radioisotope $^{18}$F has a half-life of 109 minutes, consequently time spent in purifying the composition also has an impact on issue (i). Hence, the improved composition of the third aspect is an important contributor to achieving the imaging agent composition of the first aspect.

The composition of the third aspect is preferably provided as a solution. Suitable solvents for such solution are: ethanol, aqueous ethanol, acetonitrile or aqueous acetonitrile. Preferred solvents are ethanol or aqueous ethanol, more preferably ethanol.

The composition of the third aspect may be obtained as follows. The $^{18}$F-aldehyde is diluted with ammonium hydroxide solution and then purified on an MCX mixed mode solid-phase extraction (SPE) cartridge (commercially available from Waters, part #186003516). The mixed mode cartridge has both cation exchange and reversed phase (C18) chromatography characteristics. The alkaline conditions of the crude mixture ensures that HBA, Kryptofix 222 and potassium carbonate plus any unreacted [$^{18}$F]-fluoride ion, are in ionized form. Consequently, they do not bind to the cartridge and are thus washed to waste. The [$^{18}$F]-aldehyde is subsequently eluted from the MCX cartridge with ethanol. Cationic species such as TMAB are retained by the cartridge—and not eluted when the FBA is eluted with organic solvent.

In a fourth aspect, the present invention provides a method of radiolabelling a biological targeting molecule which comprises:

(i) provision of a biological targeting moiety functionalized with an aminooxy or hydrazine group;
(ii) reaction of the functionalized-biological targeting moiety from step (i) with the radioactive aldehyde composition of the third aspect, such that the radioactive aldehyde of Formula (A) condenses with said aminooxy or hydrazine group, to give the radiolabelled biological targeting molecule.

The biological targeting moiety (BTM) of the fourth aspect, and preferred embodiments thereof are as described in the first aspect (above).

The term "amino-oxy group" is meant the BTM having covalently conjugated thereto an amino-oxy functional group. Such groups are of formula —O—NH$_2$, preferably —CH$_2$O—NH$_2$ and have the advantage that the amine of the amino-oxy group is more reactive than a Lys amine group in condensation reactions with aldehydes to form oxime ethers.

The "hydrazine group" is a functional group of formula —NH—NH$_2$.

In the method of the fourth aspect, the functionalized biological targeting moiety is preferably of Formula (IV):

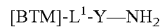

[BTM]-L$^1$-Y—NH$_2$ (IV)

and the radiolabelled product is of Formula (I):

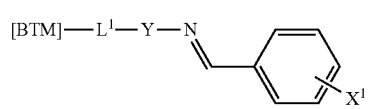

(I)

wherein:
BTM, L$^1$, Y and X$^1$ and preferred aspects thereof are as described in the first aspect (above).

The method of the fourth aspect is preferably carried out using an automated synthesizer apparatus. By the term "automated synthesizer" is meant an automated module based on the principle of unit operations as described by Satyamurthy et al [Clin. Positr. Imag., 2(5), 233-253 (1999)]. The term 'unit operations' means that complex processes are reduced to a series of simple operations or reactions, which can be applied to a range of materials. Such automated synthesizers are preferred for the method of the present invention especially when a radiopharmaceutical composition is desired. They are commercially available from a range of suppliers [Satyamurthy et al, above], including: GE Healthcare; CTI Inc; Ion Beam Applications S. A. (Chemin du Cyclotron 3, B-1348 Louvain-La-Neuve, Belgium); Raytest (Germany) and Bioscan (USA).

Commercial automated synthesizers also provide suitable containers for the liquid radioactive waste generated as a result of the radiopharmaceutical preparation. Automated synthesizers are not typically provided with radiation shielding, since they are designed to be employed in a suitably configured radioactive work cell. The radioactive work cell provides suitable radiation shielding to protect the operator from potential radiation dose, as well as ventilation to remove chemical and/or radioactive vapours. The automated synthesizer preferably comprises a cassette. By the term "cassette" is meant a piece of apparatus designed to fit removably and interchangeably onto an automated synthesizer apparatus (as defined above), in such a way that mechanical movement of moving parts of the synthesizer controls the operation of the cassette from outside the cassette, i.e. externally. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesizer. External rotation of the arm thus controls the opening or closing of the valve when the cassette is attached to the automated synthesizer. Additional moving parts of the automated synthesizer are designed to clip onto syringe plunger tips, and thus raise or depress syringe barrels.

The cassette is versatile, typically having several positions where reagents can be attached, and several suitable for attachment of syringe vials of reagents or chromatography cartridges (e.g. solid phase extraction or SPE). The cassette always comprises a reaction vessel. Such reaction vessels are preferably 0.5 to 10 mL, more preferably 0.5 to 5 mL and most preferably 0.5 to 4 mL in volume and are configured such that 3 or more ports of the cassette are connected thereto, to permit transfer of reagents or solvents from various ports on the cassette. Preferably the cassette has 15 to 40 valves in a linear array, most preferably 20 to 30, with 25 being especially preferred. The valves of the cassette are preferably each identical, and most preferably are 3-way valves. The cassettes are designed to be suitable for radiopharmaceutical manufacture and are therefore manufactured from materials which are of pharmaceutical grade and ideally also are resistant to radiolysis.

Preferred automated synthesizers of the present invention comprise a disposable or single use cassette which comprises all the reagents, reaction vessels and apparatus necessary to carry out the preparation of a given batch of radiofluorinated radiopharmaceutical. The cassette means that the automated synthesizer has the flexibility to be capable of making a variety of different radiopharmaceuticals with minimal risk of cross-contamination, by simply changing the cassette. The cassette approach also has the advantages of: simplified set-up hence reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, tamper and abuse resistance.

Included in this aspect of the invention, is the use of an automated synthesizer apparatus to prepare the radiopharmaceutical composition of the second aspect.

The method of the fourth aspect is preferably carried out in a sterile manner, such that the pharmaceutical composition of the second aspect is obtained. The radiopharmaceutical compositions of the present invention may be prepared by various methods:
(i) aseptic manufacture techniques in which the $^{18}$F-radiolabelling step is carried out in a clean room environment;
(ii) terminal sterilisation, in which the $^{18}$F-radiolabelling is carried out without using aseptic manufacture and then sterilised at the last step [eg. by gamma irradiation, autoclaving dry heat or chemical treatment (e.g. with ethylene oxide)];
(iii) kit methodology in which a sterile, non-radioactive kit formulation comprising a suitable precursor and optional excipients is reacted with a suitable supply of $^{18}$F;
(iv) aseptic manufacture techniques in which the $^{18}$F-radiolabelling step is carried out using an automated synthesizer apparatus.

Method (iv) is preferred.

Amino-oxy functionalised peptides can be prepared by the methods of Poethko et at [J. Nucl. Med., 45, 892-902 (2004)], Schirrmacher et al [Bioconj. Chem., 18, 2085-2089 (2007)], Solbakken et al [Bioorg. Med. Chem. Lett, 16, 6190-6193 (2006)] or Glaser et al [Bioconj. Chem., 19, 951-957 (2008)]. The amino-oxy group may optionally be conjugated in two steps. First, the corresponding N-protected amino-oxy carboxylic acid or N-protected amino-oxy activated ester is conjugated to the peptide. Second, the intermediate N-protected amino-oxy functionalised peptide is deprotected to give the desired product (see Solbakken and Glaser papers cited above). N-protected amino-oxy carboxylic acids such as Boc-NH—O—CH$_2$(C=O)OH and Eei-N—O—CH$_2$(C=O)OH are commercially available, e.g. from Novabiochem and IRIS.

Methods of conjugating hydrazine functional groups to polypeptides and subsequent condensations with radiolabelled aldehydes to form hydrazine-linked conjugates are described by Y. Wang et al [Nucl. Med. Biol., (2011) "Synthesis and evaluation of [$^{18}$F]exendin (9-39) . . . " epublished before print], as well as Meszaros et al [Inorg. Chim. Acta, 363(6), 1059-1069 (2010)].

The term "protected" refers to the use of a protecting group. By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Amine protecting groups are well known to those skilled in the art and are suitably chosen from: Boc (where Boc is tert-butyloxycarbonyl); Eei (where Eei is ethoxyethylidene); Fmoc (where Fmoc is fluorenylmethoxycarbonyl); trifluoroacetyl; allyloxycarbonyl; Dde [i.e. 1-(4,4-dimethyl-2,6-dioxocyclohexylidene)ethyl] or Npys (i.e. 3-nitro-2-pyridine sulfenyl). The use of further protecting groups are described in *Protective Groups in Organic Synthesis, 4$^{th}$ Edition*, Theodorora W. Greene and Peter G. M. Wuts, [Wiley Blackwell, (2006)]. Preferred amine protecting groups are Boc and Eei, most preferably Eei.

$^{18}$F-labelled aliphatic aldehydes of formula $^{18}$F(CH$_2$)$_2$O [CH$_2$CH$_2$O]$_q$CH$_2$CHO, where q is 3, can be obtained by the method of Glaser et al [Bioconj. Chem., 19(4), 951-957 (2008)]. [$^{18}$F]-fluorobenzaldehyde can be obtained by the method of Glaser et at [J. Lab. Comp. Radiopharm., 52, 327-330 (2009)]. The precursor to [$^{18}$F]-fluorobenzaldehyde, i.e. Me$_3$N$^+$—C$_6$H$_4$—CHO. CF$_3$SO$_3^-$ is obtained by the method of Haka et al [J. Lab. Comp. Radiopharm., 27, 823-833 (1989)].

Other peptides can be obtained by solid phase peptide synthesis as described in P. Lloyd-Williams, F. Albericio and E. Girald; *Chemical Approaches to the Synthesis of Peptides and Proteins*, CRC Press, 1997.

In a fifth aspect, the present invention provides a method of imaging the human or animal body which comprises generating a PET image of at least a part of said body to which the radiopharmaceutical composition of the second aspect has distributed.

Preferred aspects of the radiopharmaceutical composition and the imaging agent therein in the fifth aspect are as described in the second and first aspects of the present invention respectively (see above).

The method of the fifth aspect is preferably carried out where the part of the body is disease state where abnormal expression of the integrin $\alpha_v\beta_3$ receptor is involved, in particular where angiogenesis is involved. Such disease states include rheumatoid arthritis, psoriasis, restenosis, retinopathy and tumour growth. A preferred such diseases state of the fifth aspect is tumour growth. Positron Emission Tomography (PET) imaging of integrin $\alpha_v\beta_3$ expression is described by Beer et al [Theranostics, 1, 48-57 (2011)].

The imaging method of the fifth aspect may optionally be carried out repeatedly to monitor the effect of treatment of a human or animal body with a drug, said imaging being effected before and after treatment with said drug, and optionally also during treatment with said drug. Of particular interest is early monitoring of the efficacy of anti-angiogenic cancer therapy to ensure that malignant growth is controlled before the condition becomes terminal. Such therapy monitoring imaging is described by Battle et al [J. Nucl. Med., 52(3), 424-430 (2011)] and Morrison et al [J. Nucl. Med., 50(1), 116-122 (2009) and Theranostics, 1, 149-153 (2011)].

The method of the fifth aspect is preferably carried out whereby the radiopharmaceutical composition has been previously administered to the mammalian body. By "previously administered" is meant that the step involving the clinician, wherein the imaging agent is given to the patient e.g. as an intravenous injection, has already been carried out prior to imaging.

In a sixth aspect, the present invention provides a method of diagnosis of the human or animal body which comprises the imaging method of the fifth aspect.

Preferred aspects of the imaging agent, composition and imaging method in the sixth aspect are as described in the first, second and fifth aspects (above).

The invention is illustrated by the non-limiting Examples detailed below. Example 1 provides the synthesis of Precursor 1 of the invention. Example 2 provides the synthesis of [$^{18}$F]-FBA, and Example 3 the purification of [$^{18}$F]-FBA to obtain compositions of the invention. Example 4 provides the synthesis of Compound 1 of the invention using the purified [$^{18}$F]-FBA composition of the invention. Example 5 provides an impurity analysis demonstrating how impurity species are removed using the methods of the invention.

Abbreviations

Conventional single letter or 3-letter amino acid abbreviations are used.
Ac: Acetyl.
ACN: Acetonitrile.
Boc: tert-Butyloxycarbonyl.
DIPEA: N,N-diisopropylethylamine
DMAB: 4-(dimethyl amino)benzaldehyde.
DMSO: Dimethylsulfoxide.
EOS: End of synthesis.
FBA: 4-Fluorobenzaldehyde.
Fmoc: 9-Fluorenylmethoxycarbonyl.
HATU: O-(7-Azabenzotriazol-1-yl)-N,N,N',N'-tetramethyl-uronium hexafluorophosphate.
HBA: 4-hydroxybenzaldehyde.
HPLC: High performance liquid chromatography.
MCX Mixed mode cation exchange cartridge
NMNI: N-methymorpholine.
NMP: 1-Methyl-2-pyrrolidinone.
PBS: Phosphate-buffered saline.
PyBOP: Benzotriazol-1-yl-oxytripyrrolidinophosphonium hexafluorophosphate.
RAC: radioactive concentration.
RCP: Radiochemical purity.
RT: room temperature.
SPE: solid-phase extraction.
tBu: tert-Butyl.
TFA: Trifluoroacetic acid.
TFP: Tetrafluorophenyl.
TMAB: 4-(trimethylammonium)benzaldehyde.
$T_R$: retention time.

TABLE 1
Compounds of the Invention.
| Name | Structure |
|---|---|
| Peptide 1 | 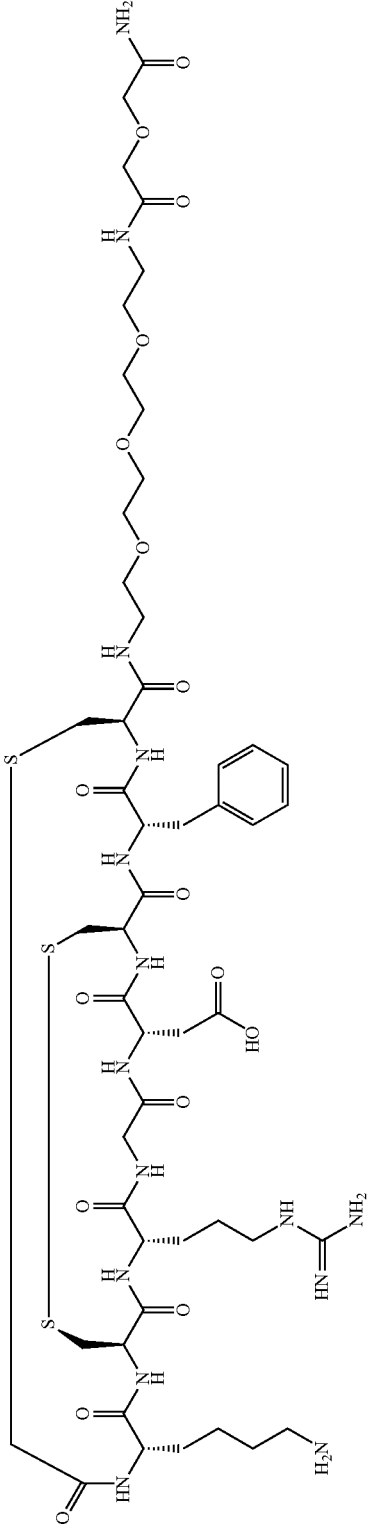 |
| Precursor 1 | 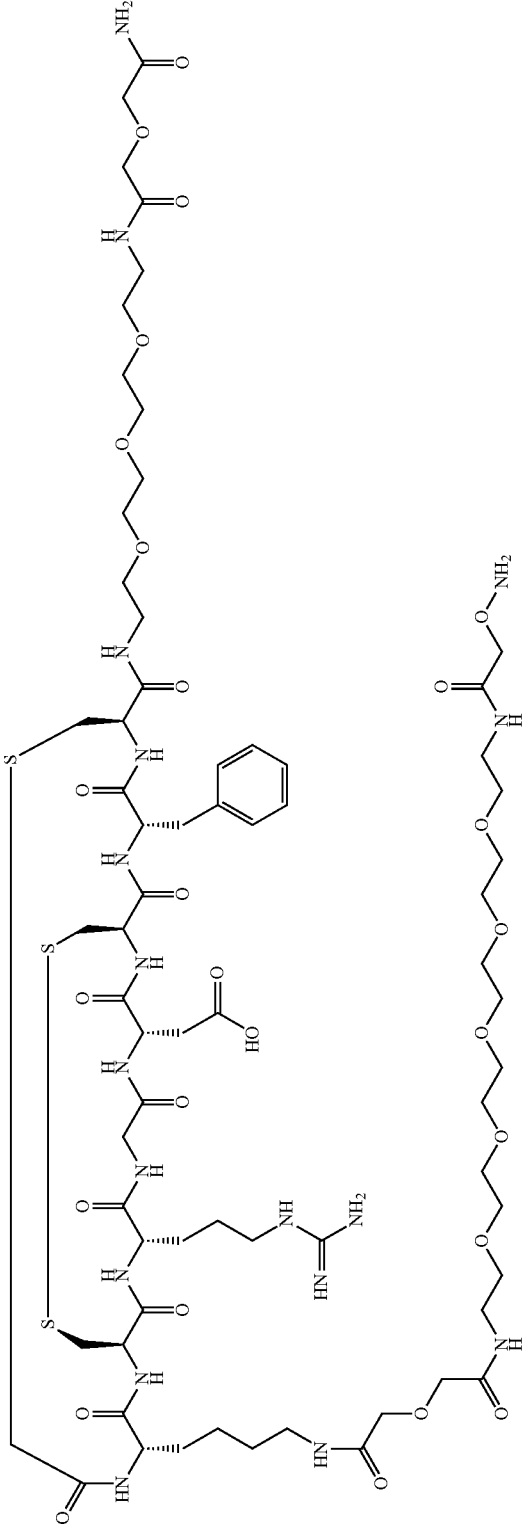 |

TABLE 1-continued

Compounds of the Invention.

| Name | Structure |
|------|-----------|
| Compound 1 | 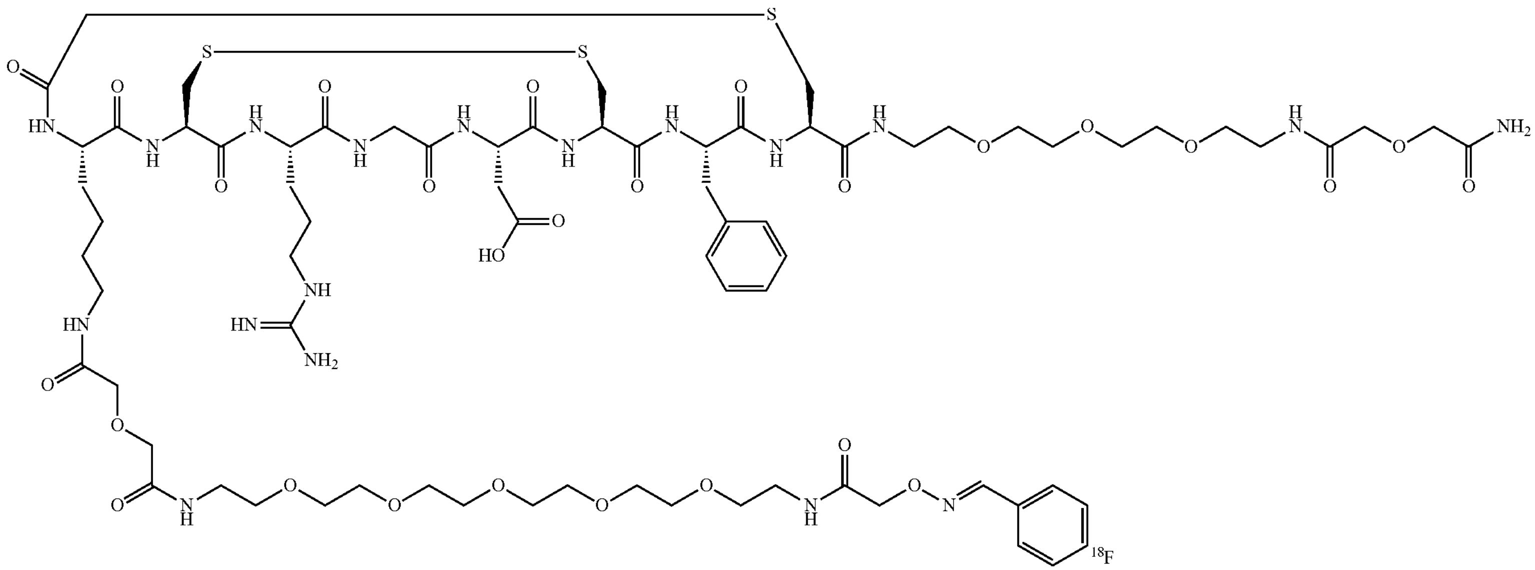 |

Example 1: Synthesis of Precursor 1

Peptide 1 was synthesised using standard peptide synthesis.

(a) 1,17-Diazido-3,6,9,12,15-pentaoxaheptadecane

A solution of dry hexaethylene glycol (25 g, 88 mmol) and methanesulfonyl chloride (22.3 g, 195 mmol) in dry THF (125 mL) was kept under argon and cooled to 0° C. in an ice/water bath. A solution of triethylamine (19.7 g, 195 mmol) in dry THF (25 mL) was added dropwise over 45 min. After 1 hr the cooling bath was removed and the reaction was stirred for another 4 hrs. Water (55 mL) was then added to the mixture, followed by sodium hydrogencarbonate (5.3 g, to pH 8) and sodium azide (12.7 g, 195 mmol). THF was removed by distillation and the aqueous solution was refluxed for 24 h (two layers were formed). The mixture was cooled, ether (100 mL) was added and the aqueous phase was saturated with sodium chloride. The phases were separated and the aqueous phase was extracted with ether (4×50 mL). The combined organic phases were washed with brine (2×50 mL) and dried (MgSO$_4$). Filtration and evaporation of the solvent gave a yellow oil 26 g (89%). The product was used in the next step without further purification.

(b) 17-Azido-3,6,9,12,15-pentaoxaheptadecanamine

To a vigorously stirred suspension of 1,17-diazido-3,6,9,12,15-pentaoxaheptadecane (25 g, 75 mmol) in 5% HCl (200 mL) was added a solution of triphenylphosphine (19.2 g, 73 mmol) in ether (150 mL) over 3 hrs at room temperature. The reaction mixture was stirred for additional 24 hrs. The phases were separated and the aqueous phase was extracted with dichloromethane (3×40 mL). The aqueous phase was cooled in an ice/water bath and the pH was adjusted to 12 by addition of solid potassium hydroxide. The aqueous phase was concentrated and the product was taken up in dichloromethane (150 mL). The organic phase was dried (Na$_2$SO$_4$) and concentrated giving a yellow oil 22 g (95%). The product was identified by electrospray mass spectrometry (ESI-MS) (MH+ calculated: 307.19. found 307.4). The crude oil was used in the next step without further purification.

(c) 23-Azido-5-oxo-6-aza-3,9,12,15,18,21-hexaoxatricosanoic acid

To a solution of 17-azido-3,6,9,12,15-pentaoxaheptadecanamine (15 g, 50 mmol) in dichloromethane (100 mL) was added diglycolic anhydride (Acros, 6.4 g, 55 mmol). The reaction mixture was stirred overnight. The reaction was monitored by ESI-MS analysis, and more reagents were added to drive the reaction to completion. The solution was concentrated to give a yellow residue which was dissolved in water (250 mL). The product was isolated from the aqueous phase by continuous extraction with dichloromethane overnight. Drying and evaporation of the solvent gave a yield of 18 g (85%). The product was characterized by ESI-MS analysis (MH+ calculated: 423.20. found 423.4). The product was used in the next step without further purification.

(d) 23-Amino-5-oxo-6-aza-3,9,12,15,18,21-hexaoxatricosanoic acid

23-Azido-5-oxo-6-aza-3,9,12,15,18,21-hexaoxatricosanoic acid (9.0 g, 21 mmol) was dissolved in water (50 mL) and reduced using H$_2$(g)-Pd/C (10%). The reaction was run until ESI-MS analysis showed complete conversion to the desired product (MH+ calculated: 397.2. found 397.6). The crude product was used in the next step without further purification.

(e) (Boc-aminooxy)acetyl-PEG(6)-diglycolic acid

A solution of dicyclohexycarbodiimide (515 mg, 2.50 mmol) in dioxan (2.5 mL) was added dropwise to a solution of (Boc-aminooxy)acetic acid (477 mg, 2.50 mmol) and N-hydroxysuccinimide (287 mg, 2.50 mmol) in dioxan (2.5 mL). The reaction was stirred at RT for 1 h and filtered. The filtrate was transferred to a reaction vessel containing a solution of 23-amino-5-oxo-6-aza-3,9,12,15,18,21-hexaoxatricosanoic acid (1.0 g, 2.5 mmol) and NMM (278 µl, 2.50 mmol) in water (5 mL). The mixture was stirred at RT for 30 min. ESI-MS analysis showed complete conversion to the desired product (MH+ calculated: 570.28. found 570.6). The crude product was purified by preparative HPLC (column: Phenomenex Luna 5 µl. C18 (2) 250×21.20 mm, detection: 214 nm, gradient: 0-50% B over 60 min where A=H$_2$O/0.1% TFA and B=acetonitrile/0.1% TFA, flow rate: 10 mL/min) affording 500 mg (38%) of pure product. The product was analyzed by HPLC (column: Phenomenex Luna 3µ C18 (2), 50×2.00 mm, detection: 214 nm, gradient: 0-50% B over 10 min where A=H$_2$O/0.1% TFA and B=acetonitrile/0.1% TFA, flow rate: 0.75 mL/min, Rt=5.52 min). Further confirmation was carried out by NMR analysis.

(f) Conjugation of (Boc-aminooxy)acetyl-PEG(6)-diglycolic acid to Peptide 1

(Boc-aminooxy)acetyl-PEG(6)-diglycolic acid (0.15 mmol, 85 mg) and PyAOP (0.13 mmol, 68 mg) were dissolved in DMF (2 mL). NMM (0.20 mmol, 20 µL) was added and the mixture was stirred for 10 min. A solution of Peptide 1 (0.100 mmol, 126 mg) and NMM (0.20 mmol, 20 µL) in DMF (4 mL) was added and the reaction mixture was stirred for 25 min. Additional NMM (0.20 mmol, 20 µL) was added and the mixture was stirred for another 15 min. DMF was evaporated in vacuo and the product was taken up in 10% acetonitrile-water and purified by preparative HPLC (column: Phenomenex Luna 5µ C18 (2) 250×21.20 mm, detection: UV 214 nm, gradient: 5-50% B over 40 min where A=H$_2$O/0.1% TFA and B=acetonitrile/0.1% TFA, flow rate: 10 mL/min,) affording 100 mg semi-pure product. A second purification step where TFA was replaced by HCOOH (gradient: 0-30% B, otherwise same conditions as above) afforded 89 mg (50%). The product was analysed by HPLC (column: Phenomenex Luna 3µ C18 (2) 50×2 mm, detection: UV 214 nm, gradient: 0-30% B over 10 min where A=H$_2$O/0.1% HCOOH and B=acetonitrile/0.1% HCOOH, flow rate: 0.3 mL/min, Rt: 10.21 min). Further product characterisation was carried out using ESI-MS (MH$_2$2+ calculated: 905.4. found: 906.0).

(g) Deprotection

Deprotection was carried out by addition of TFA containing 5% water to 10 mg of peptide.

Example 2: Radiosynthesis of $^{18}$F-Benzaldehyde ($^{18}$F-FBA)

[$^{18}$F]-fluoride was produced using a GEMS PETtrace cyclotron with a silver target via the [$^{18}$O](p,n) [$^{18}$F] nuclear reaction. Total target volumes of 1.5-3.5 mL were used. The radiofluoride was trapped on a Waters QMA cartridge (preconditioned with carbonate), and the fluoride is eluted with a solution of Kryptofix$_{2.2.2.}$ (4 mg, 10.7 M) and potassium carbonate (0.56 mg, 4.1 μM) in water (80 μL) and acetonitrile (320 μL). Nitrogen was used to drive the solution off the QMA cartridge to the reaction vessel. The [$^{18}$F]-fluoride was dried for 9 minutes at 120° C. under a steady stream of nitrogen and vacuum. Trimethylammonium benzaldehyde triflate, [Haka et al, J. Lab. Comp. Radiopharm., 27, 823-833 (1989)] (3.3 mg, 10.5 μM), in DMSO (1.1 mL) was added to the dried [$^{18}$F]-fluoride, and the mixture heated at 105° C. for 7 minutes to produce 4-[$^{18}$F]-fluorobenzaldehyde.

Example 3: Purification of $^{18}$F-Fluorobenzaldehyde ($^{18}$F-FBA)

The crude labelling mixture from Example 2 was diluted with ammonium hydroxide solution and loaded onto an MCX+SPE cartridge (pre-conditioned with water as part of the FASTlab sequence). The cartridge was washed with water, dried with nitrogen gas before elution of 4-[$^{18}$F]-fluorobenzaldehyde back to the reaction vessel in ethanol (1.8 mL). A total volume of ethanol of 2.2 mL was used for the elution but the initial portion (0.4 mL) was discarded as this did not contain [$^{18}$F]-FBA. 4-7% (decay corrected) of the [$^{18}$F] radioactivity remained trapped on the cartridge.

Example 4: Preparation of [$^{18}$F]-Fluciclatide (Compound 1)

The conjugation of [$^{18}$F]-FBA with Precursor 1 (5 mg) was performed in a solution of ethanol (1.8 mL) and water (1.8 mL) in the presence of aniline hydrochloride. The reaction mixture was maintained at 60° C. for 5 minutes.

Example 5: Impurity Analysis

The levels of benzaldehyde type impurities before and after SPE purification were determined as shown in Table 2 (based on 5250 μg of TMAB triflate salt; mol. Wt 313):

TABLE 2

| Compound | μmol |
|---|---|
| TMAB (initial) | 16.7 |
| Benzaldehydes recovered after SPE (MCX) purification | 1.5 |
| Benzaldehydes removed by SPE (MCX) purification | 15.2 |

The SPE method thus achieved removal of 91% of the impurity benzaldehydes.

What is claimed is:

1. A composition which comprises a radioactive aldehyde of Formula (A) together with one or more non-radioactive aldehydes of Formula (B):

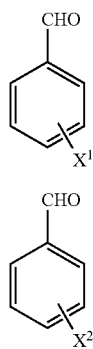

wherein $X^1$ is $^{18}F$, $-O(CH_2)_q{}^{18}F$ or $-OCH_2-CH(OH)-CH_2{}^{18}F$ and q is 2, 3 or 4;

$X^2$ is $-N^+(CH_3)_3$, $-N(CH_3)_2$, $-OCH_3$, H, $-CH_3$, $-OH$, $-SCH_3$, $-OC_6H_4CHO$ or $^{19}F$; and wherein the total concentration of Formula (B) present in the composition is greater than 0 and less than 150 µg/mL.

2. The composition of claim 1, wherein the total concentration of Formula (B) present in the composition is greater than 0 and less than 100 µg/mL.

3. The composition of claim 1, wherein $X^1$ is $^{18}F$ and $X^2$ is $-N^+(CH_3)_3$, $-N(CH_3)_2$ or $-OH$ or combinations thereof and the total concentration of Formula (B) present in the composition is greater than 0 and less than 0.83 µmol/mL.

4. The composition of claim 1, wherein $X^1$ is $^{18}F$ and $X^2$ is $-N^+(CH_3)_3$, $-N(CH_3)_2$ or $-OH$ or combinations thereof.

5. The composition of claim 1, which is provided as a solution.

6. The composition of claim 5, wherein the solution comprises the solvent ethanol, aqueous ethanol, acetonitrile, or aqueous acetonitrile.

7. A method of radiolabeling a biological targeting moiety (BTM) comprising the steps:
  (i) providing a biological targeting moiety functionalized with an aminooxy or hydrazine group;
  (ii) reacting the functionalized-biological targeting moiety from step (i) with the radioactive aldehyde composition of claim 1, wherein the radioactive aldehyde of Formula (A) condenses with the aminooxy or hydrazine group, to give the radiolabelled biological targeting moiety.

8. The method of claim 7, wherein the BTM is selected from the group of a single amino acid, a 3-100 mer peptide, an enzyme substrate, an enzyme antagonist, an enzyme agonist, an enzyme inhibitor, and a receptor-binding compound.

9. The method of claim 7, wherein the BTM is an RGD peptide.

10. The method of claim 7, wherein the BTM is a peptide having the formula:

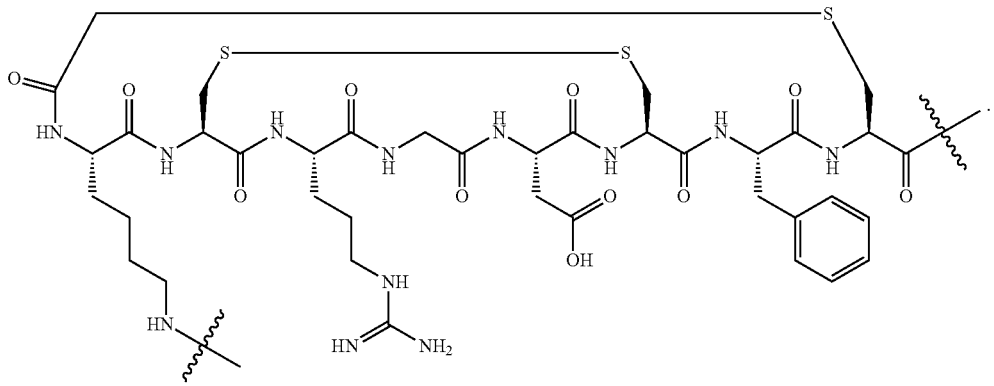 [SMILES: *NCCCC[C@@H]1NC(=O)CSC[C@@H](C(*)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]

11. A method of making the composition of claim 1, the method comprising forming the radioactive aldehyde of Formula (A) from trimethylammonium benzaldehyde followed by purifying the formed radioactive aldehyde of Formula (A) with a mixed mode cation exchange solid phase extraction (MCX+SPE) cartridge, to obtain the composition of claim 1.

12. The method of claim 11, wherein $X^1$ is $^{18}F$ and $X^2$ is $-N^+(CH_3)_3$, $-N(CH_3)_2$ or $-OH$ or combinations thereof.

13. A composition provided as a solution, the composition comprising a radioactive aldehyde of Formula (A) together with one or more non-radioactive aldehydes of Formula (B):

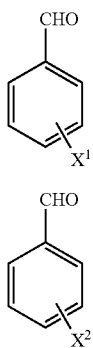

(A)

(B)

wherein where $X^1$ is $^{18}F$ and $X^2$ is —$N^+(CH_3)_3$, —$N(CH_3)_2$ or —OH or combinations thereof and wherein the total concentration of Formula (B) present in the composition is greater than 0 and less than 100 µg/mL.

14. The composition of claim 13, wherein the total concentration of Formula (B) present in the composition is greater than 0 and less than 0.83 µmol/mL.

15. The composition of claim 13, wherein the solution comprises a solvent that is selected from ethanol, aqueous ethanol, acetonitrile, and aqueous acetonitrile.

16. A method of making the composition of claim 13, comprising
forming the radioactive aldehyde of Formula (A) from trimethylammonium benzaldehyde followed by purifying the formed radioactive aldehyde of Formula (A) with a mixed mode cation exchange solid phase extraction (MCX+SPE) cartridge, to obtain the composition of claim 13.

17. The method of claim 16, wherein the total concentration of Formula (B) present in the composition is greater than 0 and less than 0.83 µmol/mL.

18. A method of radiolabel a biological targeting moiety (BTM) comprising:
(i) providing a biological targeting moiety functionalized with an aminooxy or hydrazine group;
(ii) reacting the functionalized-biological targeting moiety from step (i) with the radioactive aldehyde composition of claim 13, wherein the radioactive aldehyde of Formula (A) condenses with the aminooxy or hydrazine group, to give the radiolabelled biological targeting moiety, wherein the BTM is a peptide comprising the fragment:

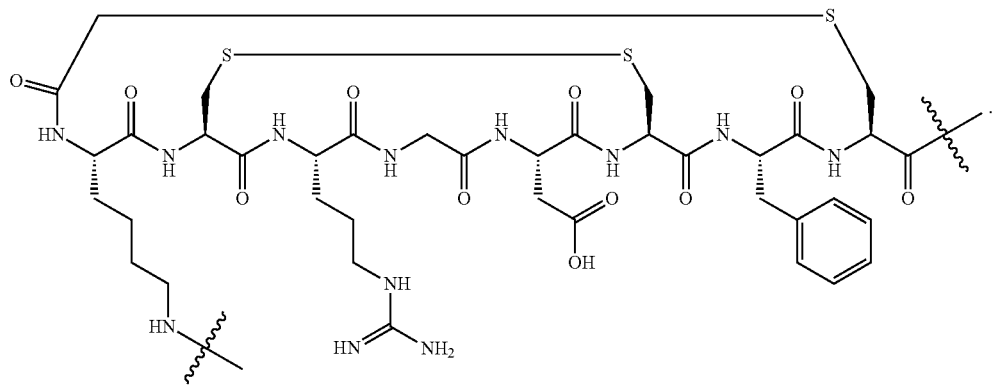 [SMILES: *NCCCC[C@@H]1NC(=O)CSC[C@@H](C(*)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]

19. The method of claim 18, wherein the BTM is precursor 1 and the radiolabeled biological targeting moiety is compound 1

Precursor 1

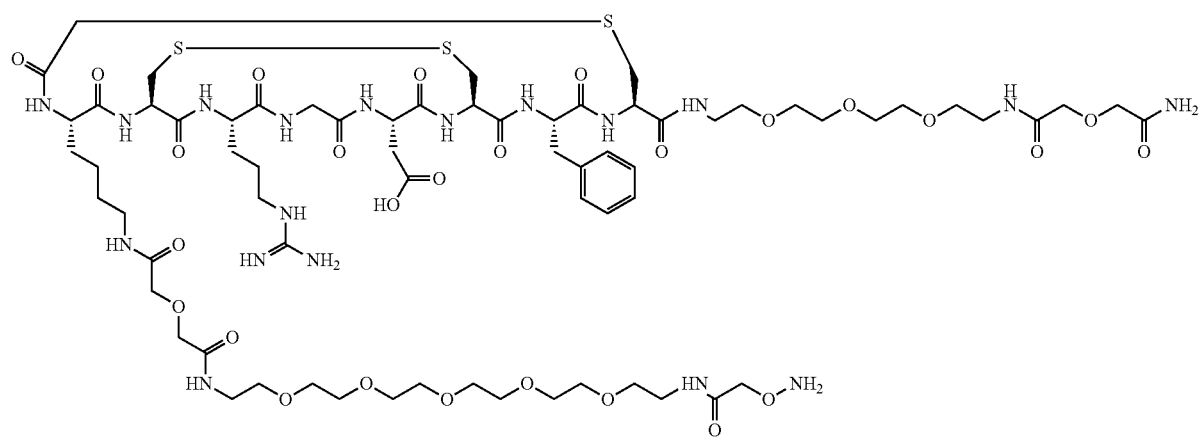

-continued
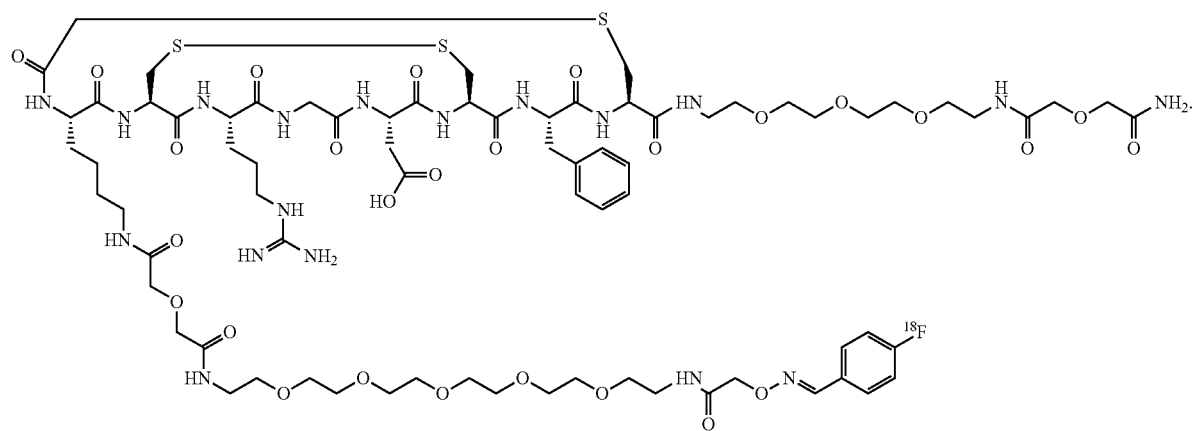
Compound 1
20. The method of claim 18, wherein the method is carried out using an automated synthesizer apparatus.
* * * * *

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial
<220> FEATURE:
<223> OTHER INFORMATION: Synthetic Peptide

<400> SEQUENCE: 1

Tyr Ile Gly Ser Arg
1               5

<210> SEQ ID NO 2
<211> LENGTH: 5
<212> TYPE: PRT
<213> ORGANISM: Artificial
<220> FEATURE:
<223> OTHER INFORMATION: Synthetic Peptide

<400> SEQUENCE: 2

Pro Asp Ser Gly Arg
1               5

<210> SEQ ID NO 3
<211> LENGTH: 5
<212> TYPE: PRT
<213> ORGANISM: Artificial
<220> FEATURE:
<223> OTHER INFORMATION: Synthetic Peptide

<400> SEQUENCE: 3

Ile Lys Val Ala Val
1               5

<210> SEQ ID NO 4
<211> LENGTH: 3
<212> TYPE: PRT
<213> ORGANISM: Artificial
<220> FEATURE:
<223> OTHER INFORMATION: Synthetic Peptide
```

```
<400> SEQUENCE: 4

Leu Arg Glu
1

<210> SEQ ID NO 5
<211> LENGTH: 15
<212> TYPE: PRT
<213> ORGANISM: Artificial
<220> FEATURE:
<223> OTHER INFORMATION: Synthetic Peptide

<400> SEQUENCE: 5

Lys Cys Gln Ala Gly Thr Phe Ala Leu Arg Gly Asp Pro Gln Gly
1               5                   10                  15

<210> SEQ ID NO 6
<211> LENGTH: 3
<212> TYPE: PRT
<213> ORGANISM: Artificial
<220> FEATURE:
<223> OTHER INFORMATION: Synthetic Peptide

<400> SEQUENCE: 6

Arg Gly Asp
1

<210> SEQ ID NO 7
<211> LENGTH: 8
<212> TYPE: PRT
<213> ORGANISM: Artificial
<220> FEATURE:
<223> OTHER INFORMATION: Synthetic Peptide

<400> SEQUENCE: 7

Asp Arg Val Tyr Ile His Pro Phe
1               5

<210> SEQ ID NO 8
<211> LENGTH: 8
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 8

Xaa Arg Val Tyr Ile His Pro Ile
1               5

<210> SEQ ID NO 9
<211> LENGTH: 8
<212> TYPE: PRT
<213> ORGANISM: Artificial
<220> FEATURE:
<223> OTHER INFORMATION: Synthetic Peptide

<400> SEQUENCE: 9

Lys Cys Arg Gly Asp Cys Phe Cys
1               5

<210> SEQ ID NO 10
<211> LENGTH: 8
<212> TYPE: PRT
<213> ORGANISM: Artificial
```

```
<220> FEATURE:
<223> OTHER INFORMATION: Synthetic Peptide

<400> SEQUENCE: 10

Lys Cys Arg Gly Asp Cys Phe Cys
1               5
```